US00PP35643P2

(12) United States Plant Patent
Doguet et al.

(10) Patent No.: US PP35,643 P2
(45) Date of Patent: Feb. 6, 2024

(54) ZOYSIAGRASS PLANT NAMED 'L1FS'

(50) Latin Name: *Zoysia matrella (L.) Merr.*
Varietal Denomination: L1FS

(71) Applicants: David Doguet, Pleasanton, TX (US); Virginia Gail Lehman, Amarillo, TX (US)

(72) Inventors: David Doguet, Pleasanton, TX (US); Virginia Gail Lehman, Amarillo, TX (US)

( * ) Notice: Subject to any disclaimer, the term of this patent is extended or adjusted under 35 U.S.C. 154(b) by 0 days.

(21) Appl. No.: 17/803,945

(22) Filed: Feb. 1, 2023

(51) Int. Cl.
*A01H 5/12* (2018.01)
*A01H 6/00* (2018.01)

(52) U.S. Cl.
USPC ..... Plt./390

(58) Field of Classification Search
USPC ..... Plt./390
See application file for complete search history.

(56) References Cited

U.S. PATENT DOCUMENTS

| | | | |
|---|---|---|---|
| PP10,636 | P | 10/1998 | Engelke |
| PP10,778 | P | 2/1999 | Engelke |
| PP11,515 | P | 9/2000 | Engelke |
| PP11,570 | P | 10/2000 | Engelke |
| PP13,166 | P2 | 11/2002 | Doguet |
| PP13,178 | P2 | 11/2002 | Doguet |
| PP14,130 | P2 | 9/2003 | Engelke |
| PP14,395 | P2 | 12/2003 | Engelke |
| PP16,982 | P3 | 8/2006 | Lehman |
| PP25,203 | P3 | 12/2014 | Doguet |
| PP28,492 | P2 | 10/2017 | Doguet |
| PP29,143 | P3 | 3/2018 | Doguet |
| PP32,805 | P3 | 2/2021 | Chandra |

*Primary Examiner* — Susan McCormick Ewoldt

(57) ABSTRACT

An asexually reproduced variety of perennial zoysiagrass with a unique combination of morphological characters including a leaf blade wider than parent 'L1F', decreased distance between tiller internodes, and soft leaf texture.

3 Drawing Sheets

Latin name of the genus and species of the plant claimed: The present invention relates to the genus and species *Zoysia matrella* (L.) Merr.

Variety denomination: 'L1FS'.

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

Field of Invention

The present invention relates to a new and distinct asexually reproduced variety of perennial zoysiagrass (*Zoysia matrella* (L.)) Merr.

BRIEF SUMMARY OF THE INVENTION

This invention relates to a new and distinct perennial zoysiagrass cultivar identified as 'L1FS' zoysiagrass (herein referred to as 'L1FS'). The inventors, David L. Doguet and Virginia G. Lehman, discovered 'L1FS' under cultivated conditions near Poteet, TX in a collection of vegetative plants derived from seed collected from 'L1F' (U.S. Plant Pat. No. 25,203) plants. 'L1FS' was identified as a distinctly different vegetative patch or clonal plant differing from the surrounding plants by having a wider leaf blade than parent 'L1F' with a short canopy height and decreased tiller vertical growth. In the plantings near Poteet, TX, 'L1FS' showed a broader leaf blade and lower canopy height compared to female parent 'L1F'. The inventors asexually reproduced 'L1FS' by taking vegetative cuttings of stolons and rhizomes, cutting the rhizomes and stolons into segments, each with a vegetative bud, and rooting them in potting media. 'L1FS' zoysiagrass will be used as a turfgrass suitable for home lawns, sports fields, and golf courses.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysiagrass plant named 'L1FS'.

BRIEF DESCRIPTIONS OF THE ILLUSTRATIONS

FIG. 1. Tiller of 'L1FS' zoysiagrass.
FIG. 2. Inflorescence of 'L1FS' zoysiagrass.
FIG. 3. Crown density and leaf texture of 'L1F' compared to 'L1FS' zoysiagrass.

COMPLETE BOTANICAL DESCRIPTION OF THE VARIETY

'L1FS' was characterized in greenhouse and field conditions. 'L1FS' is a unique variety of zoysiagrass (*Zoysia matrella* (L.)) Merr. that was discovered under cultivated conditions. The inventors, David L. Doguet and Virginia G.

Lehman, discovered 'L1FS' near Poteet, TX in a collection of vegetative plants derived from seed collected from 'L1F' (U.S. Plant Pat. No. 25,203) plants. In 2012, seeds were collected from an 'L1F' sodded area near Poteet, TX and planted in potting soil to generate five seedling plants. All five seedlings had 'L1F' as a maternal parent with the pollen parent unknown and uncontrolled to include the possibility that 'L1FS' originated as a self-pollination from 'L1F'. The five seedlings were transplanted to the field for field observation trials. In 2020, in the plantings near Poteet, TX, 'L1FS' was identified as a distinctly different vegetative patch or clonal plant differing from parent 'L1F' and other surrounding plants, with a wider leaf blade than parent 'L1F', and an extremely low vertical crown height. The plants were located in USDA Plant Hardiness Zone 8b. The inventors asexually reproduced 'L1FS' in both Poteet, TX and Amarillo, TX by taking vegetative cuttings of stolons and rhizomes, cutting the rhizomes and stolons into segments, each with a vegetative bud, and rooting them in potting media. Planting of the rooted material provided planting stock for studying performance and for comparison of morphological characters after propagation. 'L1FS' has been propagated by rhizomes, stolons, tillers, and sod. Asexually reproduced plants of 'L1FS' have remained stable and true to type through successive generations of propagation. No seedling establishment from 'L1FS' has been noticed in either greenhouse or field studies. In 2020, a vegetative increase from the clonal plot of 'L1FS' was made to a field plot of 1000 square feet to become the breeder stock of 'L1FS'.

'L1FS' is a perennial zoysiagrass that spreads by both stolons and rhizomes. Characteristics of 'L1FS' measured in 2022 and 2023 were taken from plants that were approximately 12 months in age. The greenhouse was located near Amarillo, TX, with a nighttime low temperature of 67 degrees F., and daytime high of 80 degrees F. The plants were grown with a minimum 14-hour day length, supplemented with photosynthetically active radiation equivalent to approximately 75% sunlight. The plants were fertilized with the equivalent of 1 pound of actual N per month, using a soluble fertilizer of 20-20-20 in two equal soluble applications per month.

'L1FS' has a coarser leaf texture than female parent 'L1F', putting 'L1F' in a finer leaf texture class than 'L1FS' (Table 1). 'L1FS' has an absence of leaf hairs versus 'Palisades' (U.S. Plant Pat. No. 11,515), 'Zorro' (U.S. Plant Pat. No. 14,130), 'Crowne' (U.S. Plant Pat. No. 11,570), and 'Cavalier' (U.S. Plant Pat. No. 10,778) which each have many leaf surface hairs (Table 2). 'L1FS' has shown a desirable low growing characteristic in mowed turf when compared to other zoysiagrasses of medium leaf texture such as Zeon (U.S. Plant Pat. No. 13,166)and Jackpot (not patented). The low growing or ground hugging characteristic exhibited is attributable to short internode lengths between leaves on a tiller and will manifest in culture as a reduced frequency of mowing to maintain a low canopy height. In observations, 'L1FS' showed an internode length of 6.6 mm between the $3^{rd}$ and $4^{th}$ youngest leaf (Table 3). In contrast, parent 'L1F' showed an internode length of 14.3 mm. 'L1FS' has shown little tendency to form tillers in thatch that tend towards puffiness in canopy growth in cultivars such as 'Emerald' (unpatented) that subsequently require dethatching maintenance. 'L1FS' has a slightly different leaf blade color than parent 'L1F', showing R.H.S. Colour Chart of 137A green, with 'L1F' showing 137C green in greenhouse trials. 'L1FS' has not shown susceptibility to the zoysiagrass mite when tested at Poteet, TX, where susceptible varieties have shown the coachwhip leaf symptoms of the mite. When tested at Soperton, GA, 'L1FS' showed mild susceptibility to dollar spot (*Sclerotinia honweocarpa*) and gray leaf spot (*Pyricularia grisea*). 'L1FS' has shown good turfgrass performance and temperature adaptation when tested at Soperton, GA, USDA hardiness zone 8b and at Poteet, TX, USDA hardiness zone 9a. This would suggest adaptation as far north as the southern edge of Atlanta, GA, USDA hardiness zone 8a, that would extend the area of adaptation for 'L1FS' in a line from central Georgia across central Alabama, extending through central Texas in an East/West line and on a North/South line from Norfolk, VA, south through Mexico. 'L1FS' has been exposed to low temperatures of 17 degrees F. for three consecutive days and exhibited little damage under well-watered conditions. 'L1FS' will be limited only by winter survival in colder regions. 'L1FS' is similar to most medium textured zoysiagrasses in water use demands as shown in test situations near Poteet, TX, and will be limited by adequate precipitation in drier to arid regions. 'L1FS' is adapted from sandy to heavier loam soil textures and from slightly acid to slightly alkaline soil pH.

TABLE 1

Leaf blade widths and lengths and texture class of zoysiagrasses 'L1FS' and 'L1F' (U.S. Plant Pat. No. 25,203) measured under greenhouse conditions in Amarillo, TX 2022-23.

| Variety | Leaf Stiffness | Length, 2nd youngest crown leaf cm | Width, 2nd youngest crown leaf mm | Leaf Texture Class |
|---|---|---|---|---|
| 'L1FS' | Soft | 2.1 | 1.3 | Medium |
| 'L1F' | Very Soft | 1.7 | 0.95 | Fine |

TABLE 2

Adaxial leaf hair presence or absence of selected zoysiagrass cultivars, measured under greenhouse conditions in Amarillo, TX, 2022-23.

| Variety | Leaf hair, adaxial Presence/Number |
|---|---|
| 'L1FS' | Sparse to Absent |
| 'L1F'& | Absent |
| 'Palisades'& | Many |
| 'Zorro'& | Many |
| 'Diamond'& | Absent |
| 'Royal'& | Absent |
| 'Crowne'& | Many |
| 'Cavalier'& | Many |

&'L1F' is U.S. Plant Pat. No. 25,203; 'Palisades' is U.S. Plant Pat. No. 11,515; 'Zorro' is U.S. Plant Pat. No. 14,130; 'Diamond' is U.S. Plant Pat. No. 10,636; 'Royal' is U.S. Plant Pat. No. 14,395; 'Crowne' is U.S. Plant Pat. No. 11,570; 'Cavalier' is U.S. Plant Pat. No. 10,778;

TABLE 3

Leaf and canopy characters of zoysiagrasses 'L1FS' and 'L1F' (U.S. Plant Pat. No. 25,203), measured under greenhouse conditions in Amarillo, TX, 2022-23.

| Variety | Tiller length Extension^ cm | Width, 4th youngest crown leaf mm | Internode length, leaf 1-2, 3-4 mm |
|---|---|---|---|
| 'L1FS' | 6.3 | 1.5 | 2.8, 6.6 |
| 'L1F' | 13.2 | 1.1 | 12.3, 14.3 |

^From crown height to tip of youngest leaf under unmown conditions.

TABLE 4

Canopy height at tip of youngest leaves on tillers, measured under unmown greenhouse conditions in Amarillo, TX, 2022-23.

| Variety | 18 days Regrowth Tiller Crown Height cm | 41 days Regrowth Tiller Crown Height cm | 84 days Regrowth Tiller Crown Height cm |
|---|---|---|---|
| 'L1FS' | 1.2 | 3.1 | 5.2 |
| 'L1F' | 2.3 | 6.0 | 13.3 |

TABLE 5

Winter color retention, seedhead expression, and leaf texture ratings December 2022, Poteet TX, of 'L1FS' compared to commercial and experimental zoysia cultivars.

| Variety | Color^ | Seedhead^& | Texture Class^^ |
|---|---|---|---|
| 'L1FS' | 8 | 9 | Medium |
| '685'# | 6 | 9 | Coarse |
| 'Jamur'& | 6 | 9 | Coarse |
| 'Zeon'& | 6 | 9 | Medium |
| 'DR32'# | 6.5 | 9 | Coarse |
| 'DR2'# | 6.5 | 9 | Medium to Coarse |
| 'Lazer'& | 7 | 9 | Very fine |
| 'Trinity' (L1F&) | 7 | 9 | Fine |
| 'Jackpot'# | 7 | 9 | Medium |
| 'Prizm' (M60&) | 8 | 9 | Very Fine |
| 'Stadium' (M66&) | 9 | 9 | Medium |
| LSD, p = 0.05 | 0.63 ns | | |

^Rated on a scale of 1-9, 9 = best; Rated December 2022, Poteet, TX. ^Color rating indicates winter color retention or amount of green in winter.
^&Seedhead rating on a scale of 1-9, with 9 = no seedheads present ^^Texture class based on leaf texture, mowed at 1.25 cm &'Jamur' is U.S. Plant. Pat. No. 13,178; 'Zeon' is U.S. Plant Pat. No. 13,166; 'Lazer' is 'DALZ 1308', U.S. Plant Pat. No. 32,805; 'Trinity' is 'L1F', U.S. Plant Pat. No. 25,203; 'Prizm' is 'M60', U.S. Plant Pat. No. 29,143; 'Stadium' is 'M66', U.S. Plant Pat. No. 28,492;
#'685', 'DR32', 'DR2', 'Jackpot' are not patented.

COMPLETE BOTANICAL DESCRIPTION OF THE VARIETY

Color notations for floral and vegetative characters are based on The R.H.S. Colour Chart, 2001. Light quality, photoperiod, and general growth of the plants may affect color notations.

Origin: 'L1FS' is a cultivar of a single clone discovered under cultivated conditions in a Poteet, TX planting of zoysiagrass clones derived from seeds harvested from 'L1F' *Zoysia*. In 2012, seeds were collected from a 'L1F' (U.S. Plant Pat. No. 25,203) sodded area near Poteet, TX and planted in potting soil to generate five seedling plants. All five seedlings had 'L1F' as a maternal parent with the pollen parent unknown and uncontrolled to include the possibility that 'L1FS' originated as a self-pollination from 'L1F'. The five seedlings were transplanted to the field for field observation trials. In 2020, in the turf plantings near Poteet, TX, 'L1FS' was identified as a distinctly different vegetative patch or clonal plant by having a wider leaf blade than parent 'L1F' and other surrounding plants with 'L1FS' having an extremely low vertical crown height.

Classification: *Zoysia matrella* (L.) Merr.

Mature plant height, including inflorescence: 'L1FS': 5.2 cm; 'L1F': 13.3 cm.

Growth habit: 'L1FS' is a perennial plant that spreads by stolons and rhizomes and produces a dense, low growing, medium textured turfgrass. The inflorescence of 'L1FS' is a terminal spike-like raceme, with spikelets on short pedicels.

Leaf blade: rolled in the bud, flat surface.

Leaf blade pubescence: Very sparse hair number on abaxial or adaxial leaf, as few as 1 hair per leaf, 1-2 mm in length.

Leaf sheath pubescence: Absent except for long hairs at mouth of sheath; 'L1FS' mean length sheath mouth hairs: 3.0 mm; Diamond 1.0 mm.

Leaf blade margin: 'L1FS'=entire without barbules.

Leaf blade veins: Prominent.

Leaf blade flexibility (softness): Soft.

Leaf blade color adaxial leaf surface: 'L1FS': 137A green; 'L1F': 137C green.

Leaf blade color abaxial leaf surface: 'L1FS': 137A green; 'L1F': 137C green.

Vegetative leaf, 2nd youngest vegetative leaf:

*Blade length range.*—'L1FS': 1.0 cm to 2.1 cm, mean length: 1.7 cm.

*Blade width mean.*—'L1FS': 0.7 mm to 1.88 mm, mean width: 1.7 mm; L1F: 1.0 mm.

Stolon leaf angle, third youngest leaf, measured on unmown, greenhouse grown plants: 'L1FS': 57 degrees; 'L1F': 47 degrees.

Stolon color: 161C Greyed-Yellow.

Stolon density: Less than 'L1F'; Rated on a scale of 1-9 (9=most stolons), 'L1FS': 6; 'L1F': 5; 'Meyer' (unpatented): 2;

Tendency to form puffy or clumpy turf: Rated on a scale of 1-9 (9=least puff), 'L1FS': 8; 'Emerald': 2;

Inflorescence characters:

*Culm total length, including floral area to node below flag leaf.*—3.9 cm. Length of stem of inflorescence: 2.8 cm. Floral area length: 1.1 cm.

*Culm width, stem thickness, base of floral area.*—0.4 mm.

*Culm color.*—139B Green.

*Anther length.*—0.9 mm.

*Spikelet length.*—2.1 mm.

*Spikelet width.*—0.75 mm.

*Spikelet color.*—144C Yellow Green.

*Stigma.*—155B white.

*Anther color, fresh.*—2C yellow with 187A greyed purple edges.

*Node thickness, node below flag leaf.*—0.7 mm.

*Pedicel length.*—0.3 mm.

*Flag leaf length.*—'L1FS': 2.5 mm.

*Flag leaf width.*—'L1FS': 1.0 mm.

Inflorescence emergence: 'L1FS' has sparse flowering in Poteet, TX from late April through October.

*Turf quality (rated 1-9, 9 best), mowed at fairway height.*—'L1FS': 6; 'Meyer': 3.

We claim:

1. A new and distinct variety of zoysiagrass plant, substantially as described and illustrated herein, characterized particularly by a unique combination of morphological characters.

* * * * *

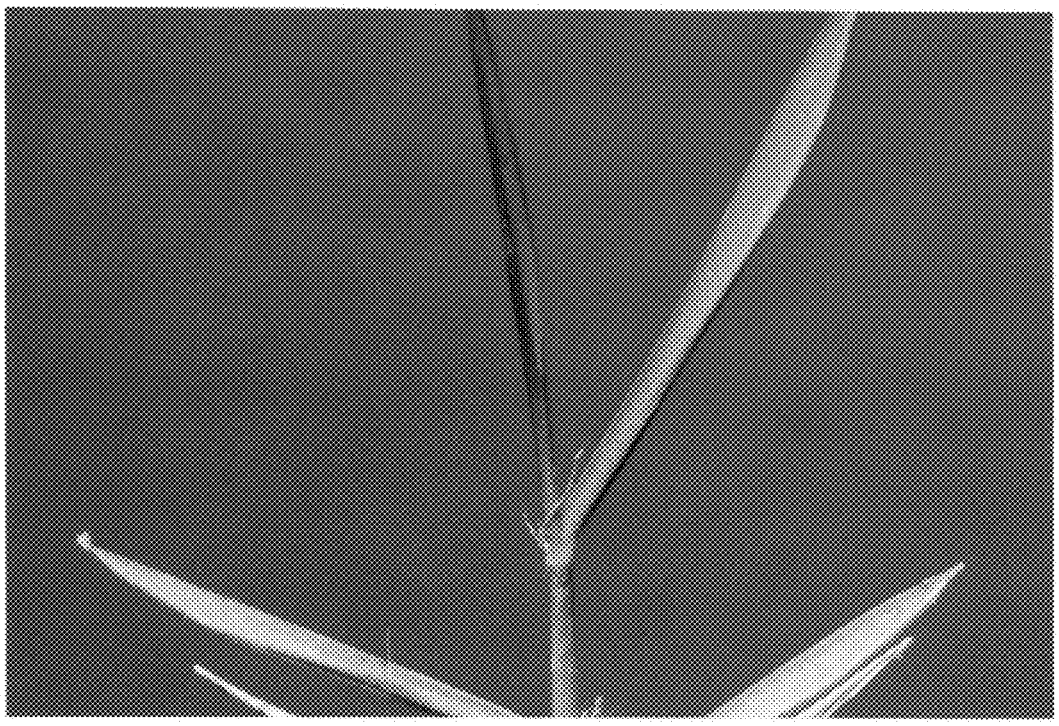
Figure 1. Tiller of 'L1FS' zoysiagrass.

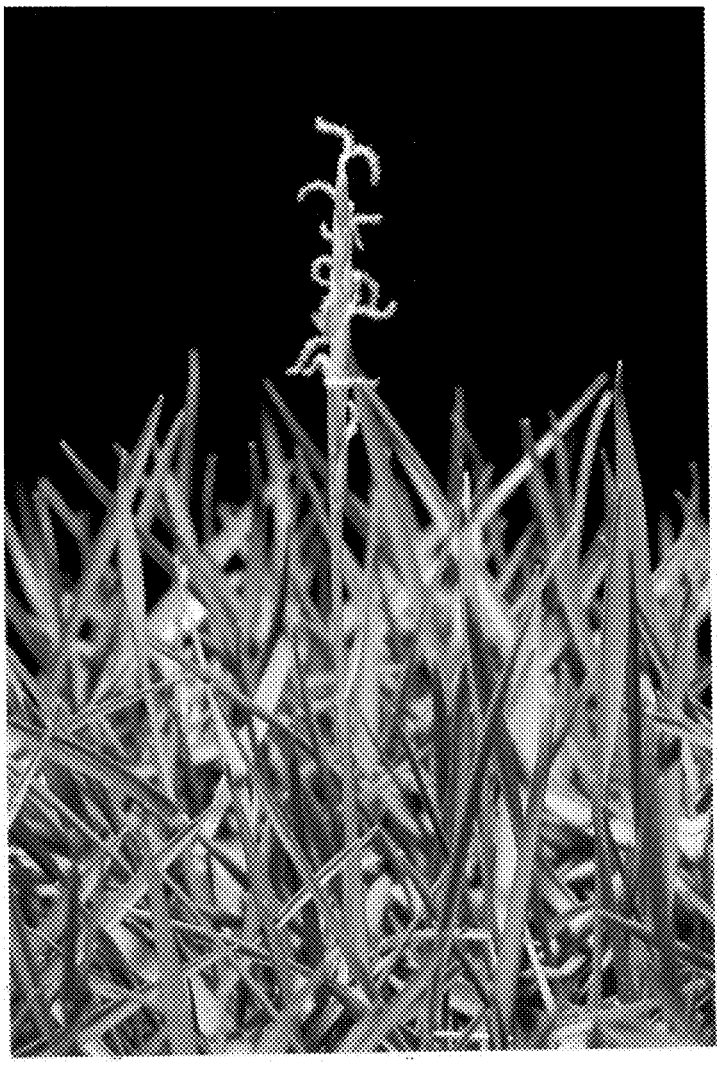
Figure 2. Inflorescence of 'L1FS' zoysiagrass.

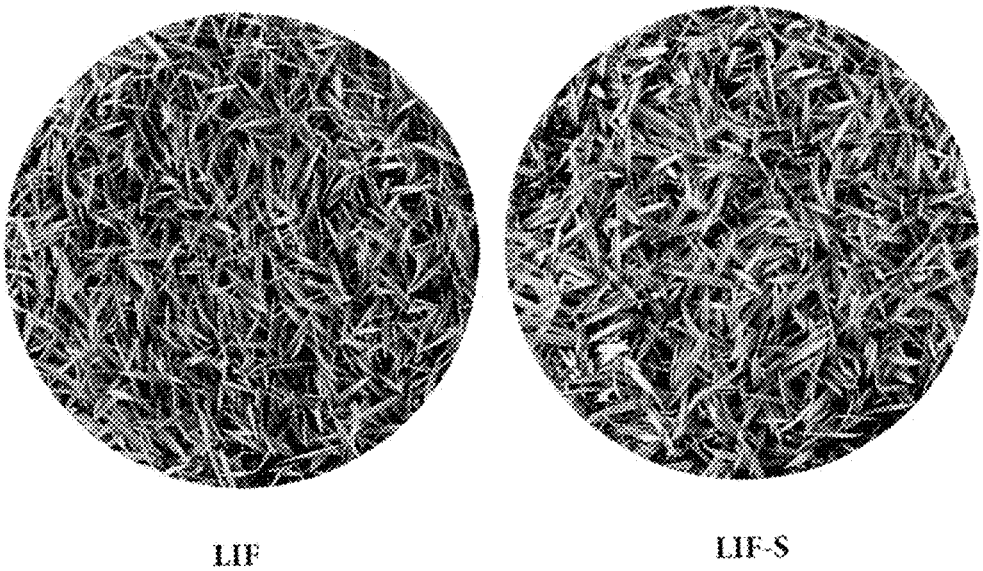
Figure 3. Crown density and leaf texture of 'L1F' compared to 'L1FS' zoysiagrass.